United States Patent [19]

Elias

[11] Patent Number: 4,475,158
[45] Date of Patent: Oct. 2, 1984

[54] MICROPROCESSOR BASED INSTRUMENT FOR DETECTING SHIFT IN BASAL BODY TEMPERATURE IN WOMEN

[75] Inventor: Andre E. Elias, Ormand Beach, Fla.

[73] Assignee: University of Florida, Gainesville, Fla.

[21] Appl. No.: 357,899

[22] Filed: Mar. 15, 1982

[51] Int. Cl.$^3$ ............... G06F 15/42; A61B 5/00
[52] U.S. Cl. ............... 364/413; 128/738; 364/557
[58] Field of Search ............... 364/413–415, 364/557; 128/736, 738

[56] References Cited

U.S. PATENT DOCUMENTS

| | | | |
|---|---|---|---|
| 4,031,365 | 6/1977 | Raggiotti et al. | 364/557 |
| 4,116,228 | 9/1978 | Hudspeth et al. | |
| 4,148,304 | 4/1979 | Mull | 128/736 |
| 4,151,831 | 5/1979 | Lester | 128/736 |
| 4,198,676 | 5/1980 | Varnum et al. | 364/557 |
| 4,396,020 | 8/1983 | Wolff et al. | 128/738 |

FOREIGN PATENT DOCUMENTS

| | | |
|---|---|---|
| 0022060 | 1/1981 | European Pat. Off. |
| 2045480 | 10/1980 | United Kingdom |
| 2066528 | 7/1981 | United Kingdom |

OTHER PUBLICATIONS

J. P. Royston and R. M. Abrams, "An Objective Method for Detecting the Shift in Basal Body Temperature in Women", Biometrics, vol. 36, No. 2, pp. 217–224, (Jun. 1980).
"Computer Aids Natural Birth Control", The Florida Times–Union–Jacksonville Journal. Saturday, Feb. 21, 1981, p. B-3, Newspaper article.
"Research at UF and in London, Paves Way for More Reliable Natural Family Planning", Press Release from University of Florida Health Center Communications, dated Friday, Feb. 20, 1981.

Primary Examiner—Errol A. Krass
Attorney, Agent, or Firm—Kerkam, Stowell, Kondracki & Clarke

[57] ABSTRACT

A portable, battery powered microprocessor-based instrument for measuring basal body temperature on a daily basis and interpreting the measurement results in accordance with a cumulative sum (CUSUM) statistical test in order to recognize a shift in basal body temperature indicative of the beginning of a period of infertility. To minimize power consumption, CMOS logic devices are employed where possible, and the instrument is turned OFF except for a brief period of two or three minutes each day. The CUSUM test involves an ongoing calculation where each day's calculations depend upon results from previous days. The instrument includes an ultra low power CMOS RAM which is continuously powered and to which all necessary data is transferred under program control prior to the conclusion of each day's program execution. A predetermined range of temperature is established within which temperature readings must be in order to be accepted as valid. This predetermined range is lower during eight baseline days for which temperatures are averaged for purposes of the CUSUM test, and higher during subsequent days when an upward shift is anticipated.

6 Claims, 7 Drawing Figures

FIG. 3B.

MICROPROCESSOR BASED INSTRUMENT FOR DETECTING SHIFT IN BASAL BODY TEMPERATURE IN WOMEN

BACKGROUND OF THE INVENTION

The present invention relates generally to natural birth control and, more particularly, to a microprocessor-based instrument for measuring basal (waking) body temperature (BBT) on a daily basis and interpreting the temperature measurement results to indicate the beginning of periods of infertility.

A known method of natural birth control is based on a recognition that basal body temperature in fertile women is variable, and normally follows a cyclical pattern, shifting upwardly near the middle of each menstrual cycle. Within a few days of the occurrance of the upward shift in temperature, sufficient time has elapsed from the occurrance of ovulation, and a period of infertility begins, knowledge of which may be utilized in a program of natural birth control.

Basal body temperature is obtained by taking a temperature measurement at a standard time which ideally is just after waking and before rising. The traditional approach involves taking daily basal body temperature readings with a conventional thermometer, recording the daily measurements in graphical form, and interpreting the graph in order to identify the occurrence of a significant upward shift in temperature.

It will be appreciated that the traditional manual approach is somewhat unreliable for a number of reasons. For one, the accuracy of the temperature reading taken by the woman is sometimes poor. Additionally, it is frequently difficult for the average person to decide when the upward shift in temperature occurs. Another reason for unreliability is that it is inconvenient for most women to take their temperature every day immediately on waking, enter the temperature reading on a graph, and spend some time studying that graph. Taking shortcuts when doing these steps compromises the quality and meaning of the results.

Accordingly, it has previously been proposed to automate the entire measurement and computation process in a portable device. For example, Letter U.S. Pat. No. 4,151,831 discloses various forms of a microprocessor-based instrument including a probe for making temperature readings, a digital clock for indicating when a temperature reading is to be taken, a memory for storing daily temperature readings, and a programmed microprocessor computing system for interpreting the results and indicating to the user when a period of infertility has begun.

Another example is disclosed in published U.K. patent application No. 80.40786, filed 19 Dec. 1980, and published as No. 2,066,528 on 8 July 1981, claiming the benefit of U.K. patent application No. 79.44063 filed 21 Dec. 1979, naming as inventors Wolff, Abrams, Royston and Everard, and entitled "Measurement of Basal Body Temperature". This British patent specification apparently corresponds to Wolff et al U.S. Pat. No. 4,396,020, issued Aug. 2, 1983. In order to reliably, and on a statistical basis, recognize the upward shift in BBT indicative of the beginning of a period of infertility, the device disclosed in the above-identified Wolff et al U.K. patent application published as 2,066,528 implements a cumulative sum (CUSUM) algorithm described in the literature: J. P. Royston and R. M. Abrams, "An Objective Method for Detecting the Shift in Basal Body Temperature in Women", *Biometrics*, Vol. 36, No. 2, pp. 217-224 (June 1980).

Underlying the development of the Royston et al algorithm described in the above-identified literature reference, and implemented in the device disclosed in the above-identified U.K. patent application, is the fact that, even with accurate daily temperature measurements, many charts depicting basal body temperature throughout a menstrual cycle do not display a sharp, clear-cut rise. Various different patterns of basal body temperature rise are found, some of which are quite difficult to interpret without benefit of hindsight. The Royston et al article describes a statistical method for detecting an upward shift in basal body temperature, which method is based on the cumulative sum (CUSUM) test previously employed in the context of quality control of production processes.

For its detailed description of the CUSUM test for detecting upward shift in basal body temperature, the above-identified Royston et al article is hereby expressly incorporated by reference. However, in order that the present invention may be better understood, the Royston et al algorithm is now briefly summarized.

The general problem is to begin with a plurality of sample values $x_1, x_2 \ldots x_r, \ldots x_N$ of a random variable X. In the context of detecting an upward shift in BBT, each of the sample values $x_r$ is simply a daily temperature reading, appropriately corrected for time of day. It is then desired to detect an upward drift of the mean $E(X)$ above some baseline B. As printed out in Royston et al, in general, menstrual cycles in which ovulation has occurred show a biphasic BBT pattern, with a shift from a low post-menstrual level to a higher level around the time of ovulation. Ovulation usually takes place about two weeks before the onset of the next menstrual period. Royston et al refer to temperatures at the lower post-menstrual level to be "pre-ovulatory", and those at the premenstrual higher level as "post-ovulatory", although it is acknowledged that the temperature change does not actually prove that ovulation has occurred.

The baseline temperature is taken as a simple average of a number of daily readings. In the instrument of the present invention, the baseline is preferably taken as a simple average of eight daily readings, commencing on the fourth day following the beginning of a menstrual period. Thus, these eight days may be considered to be a baseline period. Temperature readings for the first three days of a menstrual period are not considered valid because they are sometimes still elevated as a carryover from the previous cycle.

The actual CUSUM test for the purpose of detecting an upward shift begins following the baseline period. The temperature reading for each day is generally compared to the baseline temperature (or, more accurately, to a reference temperature R derived from the baseline temperature). Positive deviations are represented by $(x_r - R)$. The cumulative sum (CUSUM) of positive deviations will eventually become significantly large.

In the details of the implementation, a minimum change term is statistically predetermined, the minimum change term being related to the minimum basal body temperature rise considered to be physiologically significant as indicating a shift truly representative of ovulation. As reported by Royston et al, this minimum BBT rise is approximately 0.2° C. and, for purposes of the CUSUM test, the predetermined minimum change term is 0.1° C.

For purposes of comparison during the CUSUM test, rather than the actual baseline average temperature, a "central reference value" is employed, which is simply the actual baseline average temperature plus the predetermined minimum change term, which is 0.10° C. This "central reference value" corresponds to the "reference temperature" R, introduced above.

The positive deviations $(x_r - R)$ are accumulated day by day, and their cumulative sum (CUSUM) compared to a decision interval, which is also statistically predetermined. In the instrument of the present invention, the decision interval is taken as 0.25° C. On a day when the cumulative sum of positive deviations exceeds the decision interval, the CUSUM test is satisfied, indicating that a period of infertility has commenced, and the user may stop taking daily temperatures until the start of the next menstrual period.

As described in the above-identified Wolff et al U.K. patent application published as No. 2,066,528A, for improved reliability the Royston et al CUSUM test can be enhanced in two particular ways.

First, to reduce the scatter of temperature readings and thus improve the reliability of the CUSUM test, correction should be made to each temperature reading according to the time of measurement. In particular, the rate of rise of post-menstrual temperature of women before waking has been found to be close to 0.1° C. per hour between 6:00 A.M. and 10:00 A.M. Further, it is known that basal body temperature readings are valid only during the approximate period of 6:00 A.M. to 10:00 A.M.

Second, in order to reduce the probability of a false indication of infertility even though the basic CUSUM test is satisfied, it is desirable to require that, not only must the CUSUM test be satisfied, but the deviation of each individual daily temperature reading over the reference value R be positive for at least three consecutive days, including the day on which the CUSUM test is satisfied.

As further described in the above-identified Wolff et al U.K. application, it is desirable to also establish a temperature range within which temperature readings must lie in order to be accepted as valid.

Another example of such an instrument is disclosed in published European patent application No. 0,022,060, published 7 Jan. 1981, based on application No. 80.810166.1 filed 22 May 1980. This European patent application discloses a microprocessor-based system intended for use in natural birth control and including a removable remote temperature probe having its own internal memory and battery.

It will be apparent from the foregoing that several instruments generally similar to the instrument of the present invention have previously been proposed. However, the need for improvement, as a practical matter, remains.

For example, for reasons of minimal circuit complexity (and therefore cost) and flexibility in effecting fine adjustments to the algorithm parameters as additional statistical data become available, it is desirable to employ a programmable microprocessor-based instrument, for example as disclosed in Lester U.S. Pat. No. 4,151,831, rather than a hard-wired instrument as disclosed in the above-identified Wolff et al British application published as No. 2,066,528. Indeed, the specification of the Wolff et al British application recognizes that an instrument might be constructed using a microprocessor chip.

There are, however, a number of specific considerations, particularly as related to considerations of power consumption and user convenience, which are addressed in accordance with the present invention.

SUMMARY OF THE INVENTION

It is an object of the invention to provide a completely portable, self-contained, battery operated microprocessor-based instrument for measurement and interpretation of temperatures in order to reliably detect the shift in basal body temperature in women indicative of a beginning of a period of infertility.

It is another object of the invention to provide such an instrument which effectively uses a microprocessor, but which has minimal power consumption so as to prolong the life of the batteries.

It is yet another object of the invention to provide such an instrument which takes highly reliable and accurate readings, and effectively disregards readings which are invalid.

It is yet another object of the invention to provide such an instrument which is convenient to use and which requires only a minimum of user time each day.

Briefly, and in accordance with an overall concept of the invention, a low-power microprocessor-based instrument of the general type described above is provided having a number of advantages relating to power consumption, user convenience, and accuracy. To prolong battery life for reasonably extended periods, at least in excess of six months, the power consumption must be minimal. The subject instrument employs inherently low-power devices throughout, of the CMOS logic type where possible. Further, since the instrument is actually used for at most two or three minutes each day, it is normally turned OFF, and this minimizes power consumption on a long term average basis. However, the CUSUM test involves an ongoing calculation where each day's calculations depend upon results from previous days, and it is accordingly necessary to save over data from day to day. For this purpose, the instrument includes an ultra low power CMOS Random Access Memory (RAM) which is continuously powered and to which all necessary data is transferred under program control prior to the conclusion of each day's program execution, before the instrument is turned OFF. Then, when the instrument is turned ON each subsequent day, the necessary data is still available.

The only other element of the instrument which is continuously powered is a digital clock circuit which maintains correct time-of-day information at all times.

To enhance the accuracy of the instrument, a predetermined range of temperatures is established within which temperature readings must lie in order to be accepted as valid. It is important to accurately and reliably discriminate against temperature readings which might be elevated, such as by a slight fever, and yet not unnecessarily disregard valid readings. Preferably, this predetermined range of valid temperatures is not the same each day. In particular, the predetermined range of valid temperatures is lower during the eight baseline days when "pre-ovulatory" temperature readings are expected compared to the slightly higher valid temperatures possible during the days following the eight-day baseline period when "post-ovulatory" temperature readings may be expected. Preferably, the predetermined range of valid temperatures is 36.0° C. to 37.1° C. during the baseline days, and 36.0° C. to 38.0° C. thereafter. Thus, accuracy of the calculation is enhanced by providing a limited range of temperatures which are accepted as valid, and by adjusting this range in accordance with whether "pre-ovulatory" or "post-ovulatory" temperature readings are expected.

As a matter of user convenience, it is desirable to minimize the time required for a temperature reading. The time required for the thermometer probe to reach equilibrium temperature is essentially the only time required each day, as the time required for calculation each day is insignificant. Equilibrium temperature is reached in little more than one minute, and is recognized when a series of temperature readings at short intervals (e.g., ten-second intervals) have stabilized to within approximately 0.03° C. This stability criterion is based on an observation that temperature ripple following apparent equilibrium is approximately 0.02° C. (Temperature readings for CUSUM calculation purposes are interpreted with a resolution of 0.05° C. in the subject instrument.) As a result, the user is not kept waiting any longer than is necessary, as is the case with instruments which require the temperature reading to be taken for a certain number of minutes. The temperature reading may well in fact stabilize before the certain number of minutes has elapsed.

Briefly, and in accordance with a more particular aspect of the invention, a low-power microprocessor-based instrument of the general type described above is provided, and includes a battery power supply having a first supply line providing a continuous voltage, an ON/OFF switch, and a second supply line providing a switched voltage when the ON/OFF switch is ON. Within the instrument is a microcomputer including a central processing unit and a non-volatile program memory connected to the cental processing unit and powered from the switched second supply line. The microcomputer also includes a data-saving random-access memory having low power consumption connected to the central processing unit and powered from the continuous first supply line. The microcomputer, as well as other devices in the instrument, although suitable for operation from a battery for a few minutes each day, have relatively high power consumption, and would rapidly drain the battery if allowed to operate for longer periods. The data-saving memory, on the other hand is a CMOS device which can have extremely low power consumption, particularly in stand-by mode, and thus be connected to the battery power supply at all times so as to continuously maintain the data required to be saved from one to the next, and yet not unduly drain the battery. The general configuration of the instrument thus minimizes overall power consumption on a long term average basis.

The instrument additionally includes a digital clock circuit having low power consumption suitable for operation from a battery, and powered from the continuous supply line. The digital clock circuit is connected to supply data to the central processor unit.

Included in the instrument is a temperature data acquisition subsystem powered from the switched second supply line and comprising an analog-to-digital converter. The data acquisition system is connected to supply data to the central processing unit.

Also included is a user display device, preferably a low-power liquid crystal display, including a temperature reading indicator and a condition satisfied indicator. The user display device is powered from the switched second supply line and is connected to receive data from the central processing unit.

Finally, a program is stored within the non-volatile program memory and is effective, in response to operation of the ON/OFF switch to the ON position, to cause the microcomputer to execute a series of instructions for acquiring basal body temperature on a daily basis, performing a cumulative sum statistical test, and signalling when a statistically-significant shift in basal body temperature has occurred. More particularly, the instructions effect the following steps:

(1) Taking a daily temperature reading by directing the temperature data acquisition subsystem to acquire successive temperature data at predetermined intervals, and comparing each temperature datum with a previous datum until a substantially stable reading is indicated.

(2) Directing the user display device to indicate a stable temperature reading has been taken, for example, by displaying a temperature reading.

(3) Verifying whether the temperature reading is within a predetermined range of valid temperatures, and disregarding the temperature reading if outside the predetermined range of valid temperatures. Preferably, in accordance with the invention, the predetermined range of valid temperatures comprises one range during the initial eight baseline days, for example from 36.0° C. to 37.1° C., and a higher range for each day subsequent to the last baseline day, for example approximately from 36.0° C. to 38.0° C.

(4) Obtaining temperature reading time data from the digital clock circuit and verifying whether the temperature reading time is within a predetermined time window including normal waking times and within which temperature readings should be taken so as to be valid, and disregarding if the time is outside the predetermined time window. Preferably, the predetermined time window is of four hours duration, from 6:00 A.M. to 10:00 A.M.

(5) Calculating a corrected temperature reading as a function of the temperature reading time by effectively decreasing the temperature reading by approximately 0.1° C. per hour starting from the beginning of the predetermined time window.

(6) Accumulating corrected temperature readings for the predetermined number of baseline days, for example eight days, and calculating an average temperature for the baseline days.

(7) Adding a statistically predetermined minimum change term to the baseline average temperature to calculate a reference temperature. For example, the statistically minimum change term is preferably 0.1° C.

(8) For each day subsequent to the last baseline day, calculating the cumulative sum (CUSUM) of positive deviations of the corrected daily temperature readings over the reference temperature.

(9) For each day subsequent to the last baseline day, determining whether a final condition has been satisfied. The final condition is satisfied when both (A) the CUSUM has reached a statistically predetermined decision interval (for example 0.25° C.) and (B) the corrected daily temperature readings have each exceeded the reference temperature for a predetermined number of consecutive decision days. A suitable number of decision days is three days.

(10) If the final condition is satisfied, then directing the user display device to indicate conditions satisfied and otherwise storing in the data saving random-access memory, following the program execution for each day, all data necessary to initiate calculations on the following day.

It should be noted that the present invention has been described in a paper made available to the public less than one year prior to the filing date hereof. Specifically, a thesis by Andre Edward Elias entitled "A Microprocessor Based Instrument to Detect the Shift in Basal Body Temperature in Women", presented to the Graduate Council of the University of Florida in partial fulfillment of the requirements for the degree of Master of Engineering, was made available to the public in the University of Florida College of Engineering Library on Mar. 20, 1981.

BRIEF DESCRIPTION OF THE DRAWINGS

While the novel features of the invention are set forth with particularity in the appended claims, the invention, both as to organization and content, will be better understood and appreciated, along with objects and features thereof, from the following detailed description taken in conjunction with the drawings, in which:

DETAILED DESCRIPTION OF THE PREFERRED EMBODIMENT

Figure 1:
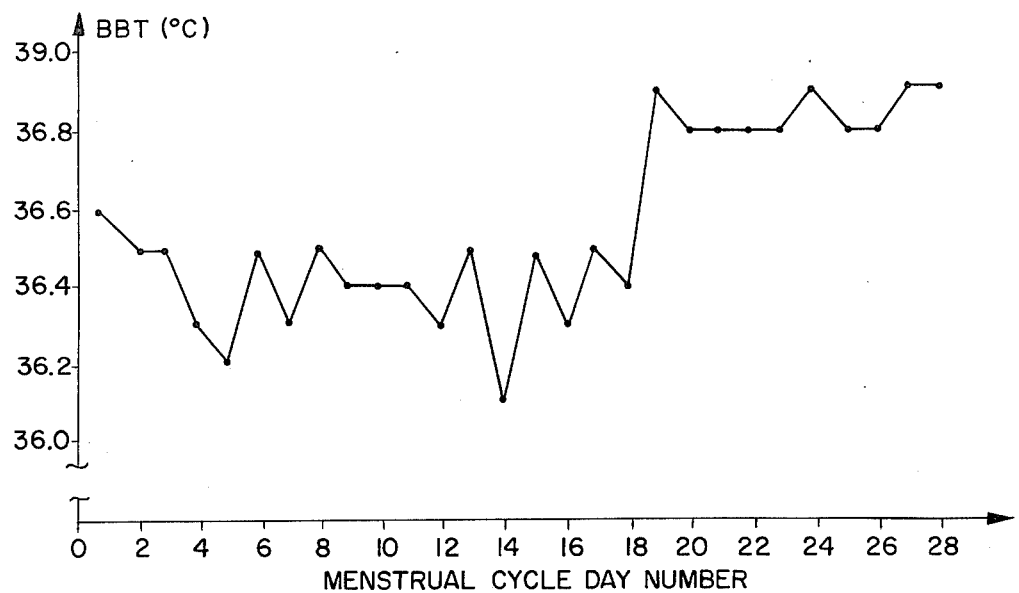
FIG. 1 is a graph comprising an easily interpretable basal body temperature chart.
Figure 2:
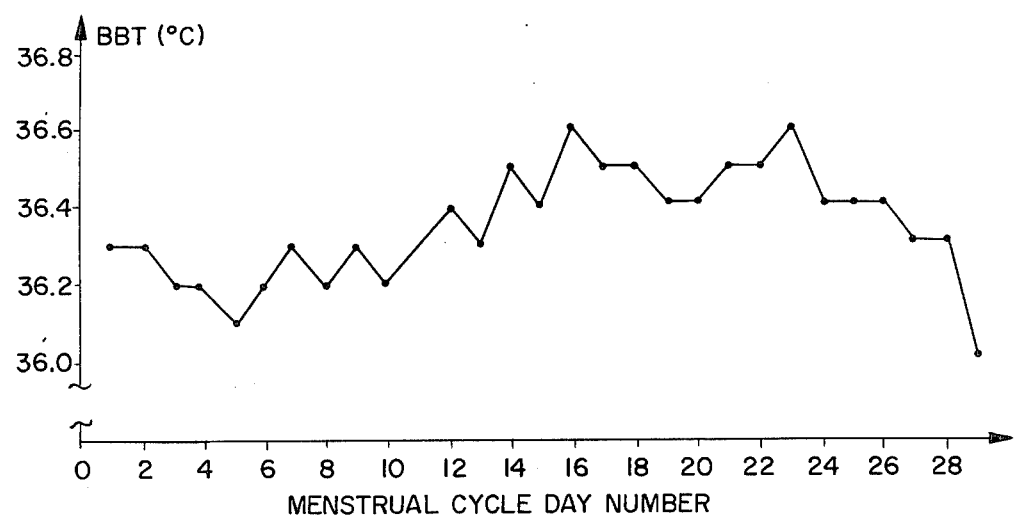
FIG. 2 is a graph comprising a more typical basal body temperature chart.

Referring first to FIGS. 1 and 2, shown are two basal body temperature charts intended to illustrate the need for a CUSUM statistical test as described by Royston et al, and implemented in the instrument of the subject invention. In these charts, basal body temperature is plotted as a function of menstrual cycle day number. FIG. 1 is an easily-interpretable basal body temperature chart exhibiting a rather sharp, clear-cut temperature rise between days 18 and 19. FIG. 2, however, is a more typical basal body temperature chart and is representative of but one of a variety of different patterns of basal body temperature shift which are found as a practical matter. It will be apparent that unaided reliable interpretation of the FIG. 2 chart would be relatively difficult, and this is one reason a statistical test such as the CUSUM test is preferably employed.

Figures 3A, 3B:
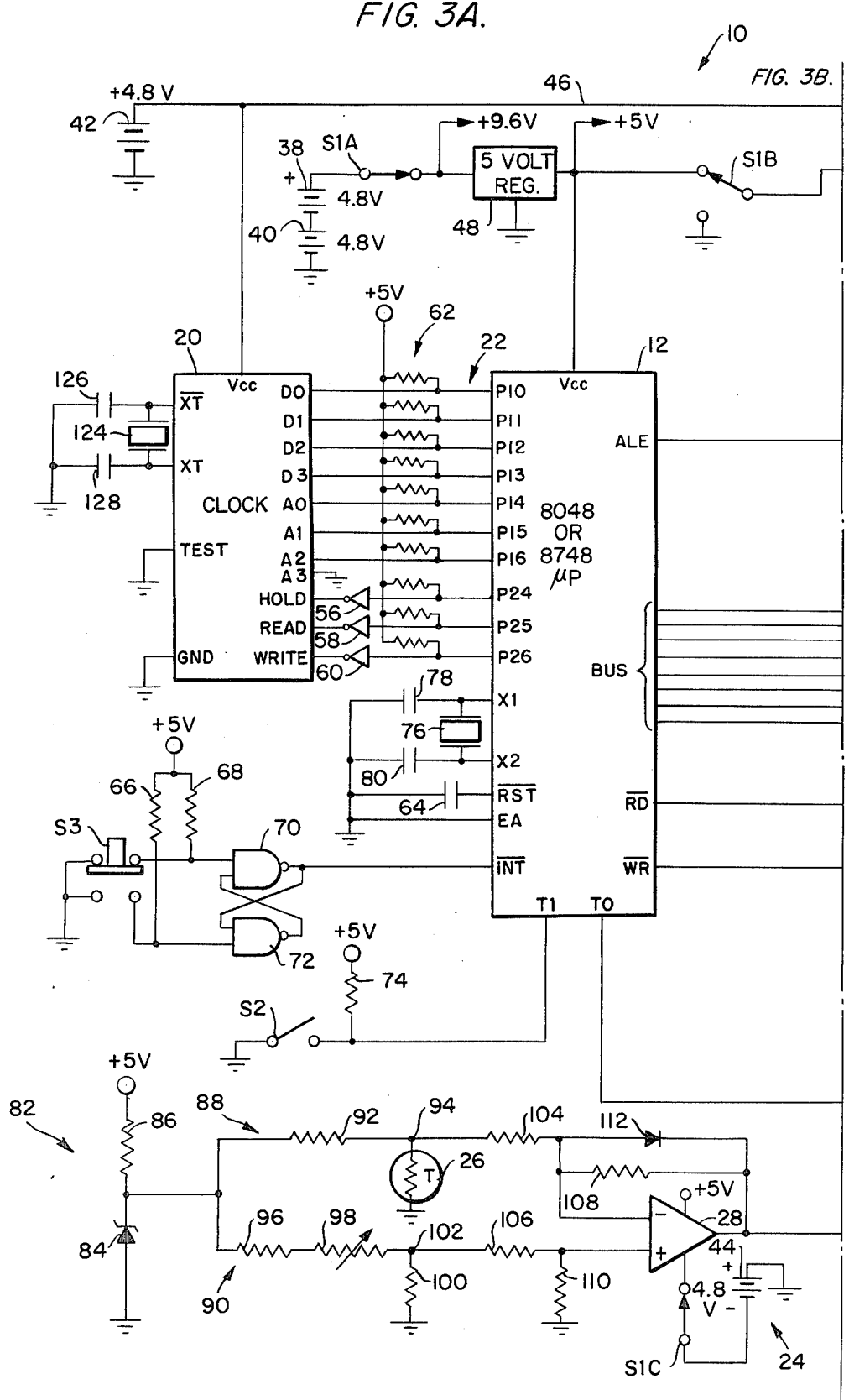
FIGS. 3A and 3B, when placed side-by-side, are a detailed electrical schematic diagram showing the hardware of the instrument of the present invention.
Figure 3B:
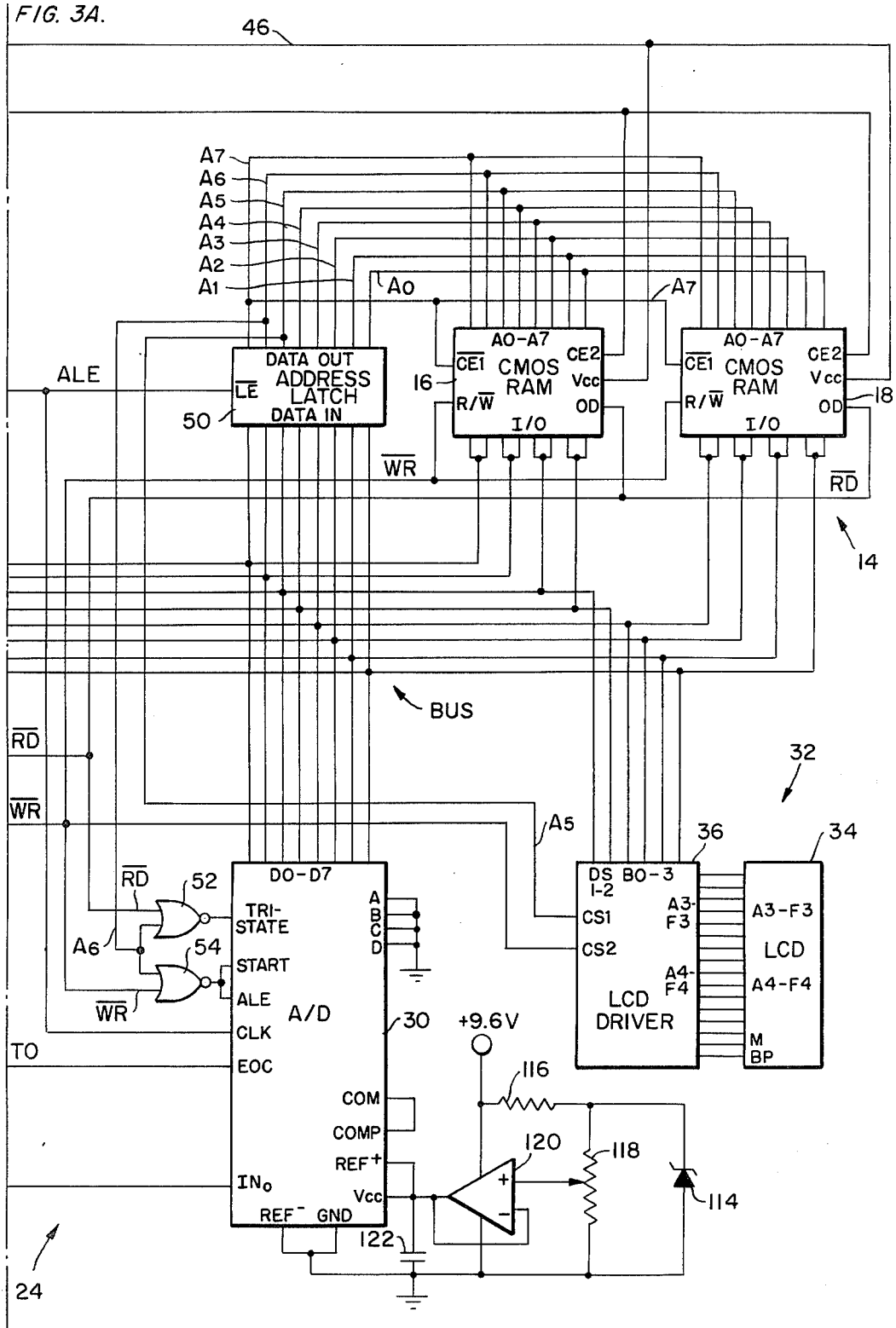

With reference now to FIGS. 3A and 3B, the instrument hardware takes the form of a specialized microcomputer system 10 comprising a single-chip microcomputer 12. Preferably, the microcomputer 12 is one of the 8048 series microcomputers manufactured by Intel Corporation. Specific type numbers especially suitable are Type No. 8048 which has an on-board 1024 byte read-only memory (ROM) for program storage, and the essentially equivalent Type No. 8748 which has an on-board 1024 byte electrically programmable read-only memory (EPROM) for program storage. The Type No. 8048 and 8748 microcomputers include, in addition to the 1024 byte program memory, an eight bit central processing unit (CPU), a clock oscillator requiring an external crystal, a timer, and a 64 byte random-access scratch pad memory, a number of locations of which are utilized as general purpose registers. A particularly advantageous feature of the 8048 and 8748 is a relatively large number of input/output lines, twenty-seven in all, which facilitates direct connection to various other devices in the microcomputer system 10.

Figure 4:
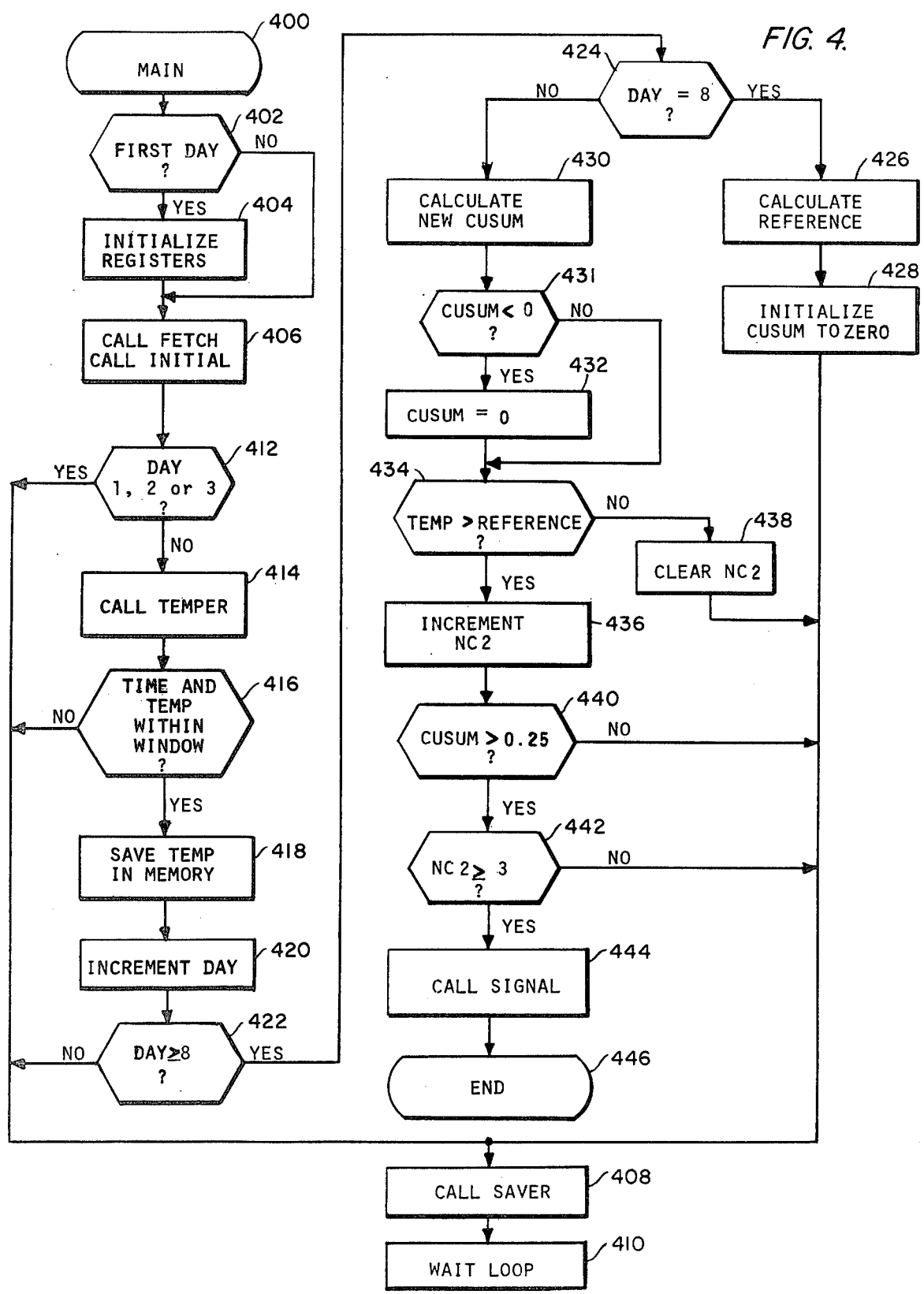
FIG. 4 is a program flow chart depicting program "MAIN" resident in the microprocessor program memory.
Figure 5:
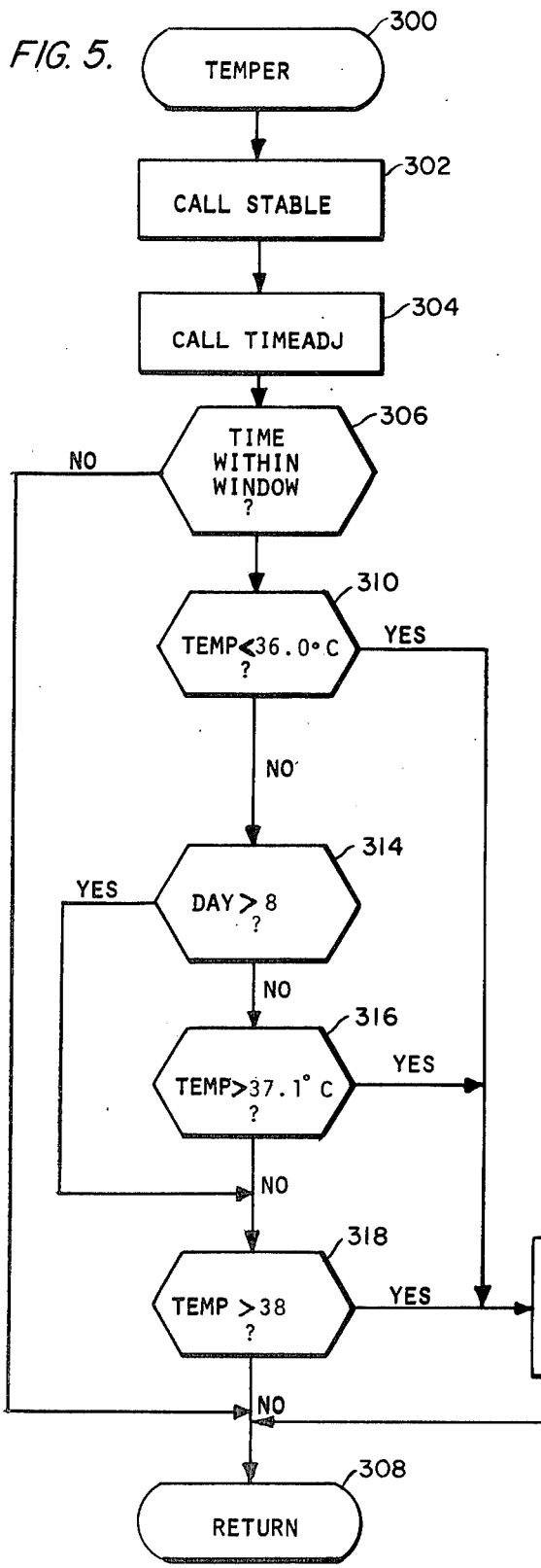
FIG. 5 is a program flow chart of subroutine "TEMPER" also resident within the program memory.
Figure 6:
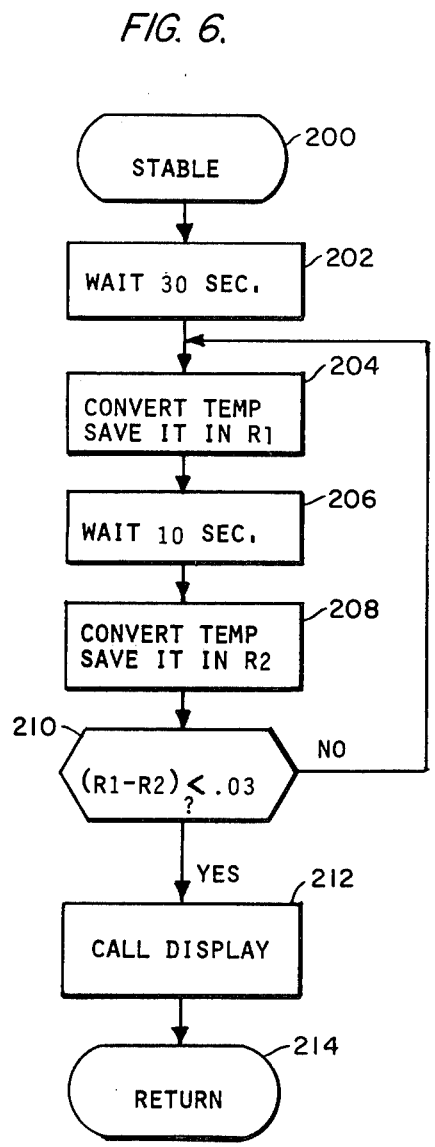
FIG. 6 is a program flow chart of subroutine "STABLE" resident within program memory.

The main task of the microcomputer 12 in the system 10 is to implement the CUSUM algorithm. FIGS. 4–6, described hereinafter, give a flow chart description of several important routines of the program, and a complete assembly language program listing of all routines comprising the program is provided hereinafter. This program resides in the program memory of the microcomputer 12, from location $0_{16}$ to $3FF_{16}$.

Closely associated with the microcomputer 12 is an external random-access memory 14 used particularly as a data memory. The random-access memory 14 is always powered and thus always retains stored data. The memory 14 employs CMOS devices for extremely low power consumption, particularly in the standby mode. Preferably, the external random-access memory 14 comprises a pair of Type No. 5101 256×4 bit static CMOS RAM's 16 and 18 which have a maximum combined current consumption of 54 milliamperes during active operation, and only 20 microamperes during standby. The 5101 devices may be classified as ultra-low power, ideal for continuous battery operation.

Another element of the microcomputer system 10 is a digital clock circuit 20 which generates time of day information in clock format, and makes this information available to the microcomputer 12 via a bus 22 connected to input terminals P10 through P16, which together comprise Input/Output Port 1 of the microcomputer 12.

Also included in the microcomputer system 10 is a temperature data acquisition subsystem 24 including a thermistor temperature sensor 26, an operational amplifier 28, and an analog-to-digital converter 30.

Finally, the specialized microcomputer system 10 includes a user display device 32 comprising a liquid crystal digital display 34 and a liquid crystal display driver 36.

The various subsystems just identified are appropriately connected together through various data and address busses, and each is described hereinafter in detail.

An important feature of the instrument 10 is its low power consumption. In order to use the minimum amount of power, most of the circuitry, including the microprocessor 12, is turned ON for only two or three minutes each day, during the actual temperature measurement. However, the program starts at the beginning of each menstrual cycle, and does not terminate until an upward shift in basal body temperature is detected, many days later. Therefore, it is necessary for data to be saved even while the microcomputer 12 is turned OFF. In accordance with the invention, the necessary data is saved in the CMOS memory devices 16 and 18.

Four 4.8 volt mercury batteries 38, 40, 42 and 44 supply power to the instrument 10, and together comprise a battery power supply. There are two devices in the instrument 10 which require a continuous supply of power, the clock chip 20 and the random-access memory 14 comprising CMOS devices 16 and 18. Power to all other devices is switched. Accordingly, the battery power supply has a first supply line 46 connected directly to the battery 42 and providing a continuous voltage to the $V_{CC}$ terminals of the clock chip 20 and the memory devices 16 and 18. The clock chip 20 is preferably a Type No. MSM5832 CMOS device, and consumes a maximum of only 500 microamperes at 5 volts. As stated above, the two CMOS memory devices 16 and 18 require a total of only 20 microamperes for data retention in standby mode.

The battery power supply also includes an ON/OFF switch comprising ganged sections S1A, S1B and S1C, all shown in the ON position, supplying various second supply lines when the ON/OFF switch is ON. Most of the devices in the system 10 require +5 VDC, which is supplied through a conventional three-terminal voltage regulator 48.

Since the CMOS RAM devices 16 and 18 together draw only 20 microamperes for data retention in standby mode, but up to 50 milliamperes when active, it is important that they be positively placed in standby mode when the instrument is OFF. For this purpose, a Chip Enable input (CE2) from each of the two RAM devices 16 and 18 is selectively connected through ON/OFF switch section S1B to either +5 Volts or circuit ground. With the instrument OFF, the CE2 inputs are at logic low.

This power supply arrangement advantageously meets the needs of the subject circuit. The microcomputer 12 is the most complicated integrated circuit in the instrument and consumes the largest amount of power. The maximum power supply current for a Type No. 8748 is 135 milliamperes. However, this current is drawn from the batteries 38 and 40 through the 5 volt voltage regulator 48 only when the instrument is turned ON, which occurs for only a few minutes each day.

Immediately below are described a number of aspects of the 8048 or 8748 microcomputer 12 in the particular context of the subject invention, followed by a more detailed description of the Liquid Crystal Display 34 and Driver 36, and the temperature data acquisition subsystem 24 and the clock chip 20. The 8048 or 8748 microcomputer 12 is described below only briefly, and reference should be had to the manufacturer's data sheet and various other publications for a detailed description of the microprocessor and their programming.

There are three distinct memories utilized in the subject system employing an 8048 or 8748 microcomputer. The first memory is the on-chip (internal) program memory. This is a non-volatile $1024 \times 8$ bit memory of either ROM (for the 8048) or EPROM (for the 8748) type. Although the 8048 and 8748 microcomputers have provisions and addressing capability for external program memory, only internal program memory is used in the subject system, and the External memory Access (EA) pin is grounded. Program memory is normally addressed via an internal 12-bit program counter.

The second memory is the on-chip (internal) Random Access Memory used as a general purpose scratchpad, and as general purpose registers directly accessible by various instructions. In the subject system, registers R0 through R7 are used extensively. Significantly, since the on-chip RAM is a volatile memory, the data stored in registers R0 through R7 is lost whenever power to the microcomputer 12 is turned OFF, as it is except for the minute or so each day during active temperature measurement and computation. The on-chip RAM is generally accessed by "MOV" mnemonic instructions, with the memory address being indicated by the contents of register R0 or R1, in addition to being accessed by various special register instructions.

The third memory is the external random-access memory 14 comprising CMOS devices 16 and 18. These are always powered. It is a feature of the present invention that, upon completion of each day's temperature measurement and program execution, data from several of the registers is stored in the external memory before power is removed from the microcomputer 12. At the beginning of program execution for each subsequent day, the data is retrieved from the external memory and put back in the registers. Additionally, some data is immediately stored directly in the external random-access memory 14, in particular, the daily temperature readings during the eight-day baseline period. The external RAM 14 comprising devices 16 and 18 is generally accessed by "MOVX" mnemonic instructions, with the memory address being indicated by the contents of register R0 or R1.

Input to and Output from the 8048 or 8748 microcomputer 12 is through three Ports, as well as through a variety of specialized Inputs and Outputs. These are all advantageously utilized in the system of the present invention for minimal chip count and complexity.

The primary Input/Output Port is a bidirectional 8-bit BUS port. The 8-bit BUS port serves as a time-multiplexed Data and Address Bus. Since the BUS is time multiplexed, an address latch 50 is required, which is preferably a Type No. MM74C373 CMOS Octal D-type transparent latch. For data transfer purposes, the BUS is connected directly to the data input and output lines of the external RAM 14 comprising devices 16 and 18, the analog-to-digital converter 30, and to the Liquid Crystal Display Driver 36. For addressing purposes, the BUS is connected through the Address Latch 50 to these same devices.

Three output control pins of the 8048 or 8748 microcomputer 12 control external data and address operations on the BUS.

First, the Address Latch Enable (ALE) output is connected to the Latch Enable ($\overline{\text{LE}}$) input of the address latch 50. ALE is pulsed high at the beginning of every instruction execution machine cycle, and the trailing edge of ALE strobes the address data on the BUS into the address latch 50, the outputs of which then maintain the address so long as ALE, and thus $\overline{\text{LE}}$, are low. The address output lines of the address latch 50 are designated $A_0$ through $A_7$, with $A_0$ being the least significant address bit.

Second, the data memory Read control ($\overline{\text{RD}}$) output, which is pulsed low to strobe data from the external devices onto the BUS, is connected to the CMOS RAM devices 16 and 18, and to the TRI-STATE input of the Analog-to-Digital converter 30 via a NOR gate 52. The other input of the NOR gate 52 is connected to the output of the Address Latch 50, specifically, to the line carrying address bit $A_6$.

Third, the data memory Write control ($\overline{\text{WR}}$) output, which is strobed low when external devices are to take data off the BUS, is connected to the CMOS RAM devices 16 and 18 ($R/\overline{W}$) inputs, to the Analog-to-Digital converter 30 via a NOR gate 54 also having its other input connected to the $A_6$ output of the Address Latch 50, and to a Chip Select (CS1) input of the LCD Display Driver 36.

Although the two type 5101 RAM's 16 and 18 together have an apparent capacity of 256 bytes, this is not all needed. In order to minimize the external hardware, the most significant bit ($A_7$) of the address from the latch 50 is used to enable the RAM's 17 and 18 ($\overline{\text{CE1}}$ input), so that external data memory is actually addressed from locations 0 to $127_{10}$.

The other two Input/Output Ports are secondary I/O Port 1 and Port 2. Port 1 comprises Pins P10–P17, of which only P10–P16 are utilized in the subject system. Port 2 comprises Pins P20–P27, of which only P24–P26 are utilized in the subject system. Pins P10–P16 are connected directly to the clock chip 12, and Pins P24–P26 are connected to the clock chip 12 through inverters 56, 58 and 60. The pins P10–P16 and P24–P26 have individual pull-up resistors 62 connected to +5 volts.

Four specialized inputs of the microcomputer 12 are advantageously utilized in the subject system. These are Reset ($\overline{RST}$), external Interrupt ($\overline{INT}$) and Test inputs T0 and T1.

The Reset ($\overline{RST}$) input, when pulled low, forces the internal program counter to program memory location 0, at which execution then begins. The $\overline{RST}$ input is simply connected through a capacitor 64 to circuit ground. Upon power up, the capacitor 64 functions as a differentiator to provide a momentary logic low pulse, thus resetting the microcomputer 12.

The external Interrupt ($\overline{INT}$), when enabled and pulled low, forces a jump (actually a subroutine call) to program memory location 3, at which execution then continues. This $\overline{INT}$ input is advantageously used in the subject instrument for re-initializing the clock chip 20 to 8:00 AM at any time, particularly after battery replacement or upon a time zone change. In such event, subroutine TIMESET, listed hereinafter, is called after a jump to program memory location 3. Specifically, a momentary pushbutton timeset switch S3 is connected through a de-bounce network comprising pull-up resistors 68 and 68 and a pair of cross-coupled NAND gates 70 and 72 to and the $\overline{INT}$ input. With the timeset switch S3 in the normal position shown, $\overline{INT}$ is high. When the timeset switch S3 is actuated, $\overline{INT}$ is pulled low.

The Test inputs T0 and T1 are sampled by the microcomputer 12 via conditional jump instructions. Instruction mnemonic "JT0" causes a jump if input T0 is high, and instruction mnemonic "JT1" causes a jump if input T1 is high.

The Test input T1 is advantageously used in the subject instrument for indicating the first day of a menstrual period at which the entire CUSUM algorithm must be re-initialized to Day 1, and all counter registers initialized. Specifically, a pull-up resistor 74 is connected to Test input T1 to establish a normal logic high condition indicating a particular day is not the first day. An SPST "First Day" switch S2 is connected to pull Test input T1 low on the first day. In operating the instrument, the "First Day" switch S2 is closed on the first day, before the instrument is turned ON. Near the beginning of program execution input T1 is tested and, if low, the registers are appropriately initialized for Day 1.

The Test input T0 is advantageously utilized in the subject instrument to determine the end of an analog-to-digital conversion operation. Test input T0 of the microcomputer 12 is connected directly to the End of Conversion (EOC) output of the analog-to-digital converter 30.

The two remaining inputs to the microcomputer 12 are connections X1 and X2 to an external quartz crystal 76 which establishes the frequency of the internal microcomputer 12 clock oscillator. Capacitors 78 and 80 are part of the oscillator circuit.

In order to display the temperature each day, and also to display an acknowledgement signal (a blinking colon) when the upward shift in temperature is detected, as well as to minimize the power consumption of the circuit, the Liquid Crystal Display (LCD) 34 is used, which is an entirely conventional four-digit LCD. The LCD Driver 36 preferably is an Intersil Type No. ICM 7211, a four-digit LCD decoder-driver, interfaced to the microprocessor 12 and to the LCD 34. One line from the latched address bus (address bit $A_5$) and the $\overline{WR}$ strobe output of the microcomputer 12 are used to select the LCD decoder-driver 36. The data output lines and the digit-select lines of the ICM 7211 decoder-driver 36 are connected to the bidirectional BUS of the 8748, so that the Display 32 can be considered as a memory mapped Input/Output device. Data is outputted to a Display 32 using the MOVX instruction. The hexadecimal code of the digit to be displayed and the code for the digit select lines are stored in the microcomputer accumulator and then written to external data memory by properly selecting the LCD decoder-driver 36.

The ICM 7211 is not time multiplexed, so the software controls the display of the four different digits. Subroutine "DISPLAY", listed hereinafter, does this.

The temperature data acquisition subsystem 24 functions to take the temperature from the thermistor 26 as an input, digitize this temperature and present the digital data to the microcomputer 12. The data acquisition subsystem 24 comprises the thermistor 26, the amplifier 28, and the eight-bit analog to digital converter 30.

The thermistor 26 is included in a circuit 82 supplied with a stable reference voltage of 1.240 volts provided by a Zener diode 84 and series resistor 86 connected to the +5 Volt switched source. The thermistor circuit 82 comprises two branches, a thermistor branch 88 and a reference branch 90. The thermistor branch 88 comprises the thermistor 26 and a series resistor 92 connected in voltage divider configuration to provide an output voltage at a node 94. The reference branch 90 comprises series resistors 96, 98 and 100 connected in adjustable voltage divider configurations to provide a reference voltage at a node 102.

The thermistor 26 is a YSI Type No. 44104 sealed in an aluminum tube (not shown) for protection and to provide a probe configuration. The thermistor 26 time constant in still air is twenty-five seconds; however, this time constant increases to thirty to forty-five seconds when the thermistor 26 is used in the oral cavity, with the aluminum shield. While thermistor 26 operates between −80° C. and +180° C., the only temperatures to be measured are between 36° C. and 38° C. The optimum value of the series resistance 92 which makes the voltage across the thermistor linear with respect to temperature over this narrow range was calculated, and found to be 1000 ohms.

The operational amplifier 28 is a Harris Type No. HA2700, which is an internally compensated operational amplifier characterized by excellent DC and dynamic performance with very low quiescent power consumption. The amplifier 28 has a pair of series input resistors 104 and 106 connected respectively to the thermistor branch node 94 and the reference node 102, and amplifies the difference. A resistor 108 provides negative feedback to the inverting (−) input to establish the amplifier gain, and a biasing resistor 110 is connected between the non-inverting (+) input and circuit ground. The output of the amplifier 28 is connected to the $IN_0$ input of the analog to digital converter 30, which has an allowable input voltage range of 0 to 5.120 volts. In the illustrated circuit, an amplifier voltage gain of eighty-two was found to be suitable, and is achieved by selecting the ratio of the negative feedback 108 to the input resistor 104.

In order to maintain the amplifer 28 output signal positive at all times to avoid possible damage to the A/D converter 30, a switching diode 112 is included in the operational amplifier negative feedback loop, in parallel with the resistor 108. Connection of the diode 112 in the negative feedback loop minimizes the power consumption of the circuit, since the current inside the feedback loop is negligible.

Tests have shown that the temperature data acquisition subsystem 24 meets or exceeds all requirements for stability, linearity, and resolution. Resolution is well within the 0.05° C. requirement.

The analog-to-digital converter 30 is a National Semiconductor Type No. ADC0816. The ADC0816 includes a 16-channel analog multiplexer and a successive approximation 8-bit analog-to-digital converter. Moreover, the ADC0816 is a CMOS device with low power consumption (the maximum current requirement is only 3 milliamperes), and it is microprocessor compatible: the channel address can be latched and decoded, the control signals are TTL compatible, and the data output can be latched and tristated.

To provide the reference voltage for the analog to digital converter 30, a National LM328 precision temperature compensated zener diode 114 is employed with a series current-limiting resistor 116 connected to the switched +9.6 Volt DC provided by the batteries 38 and 40. A potentiometer 118 is included to adjust the reference voltage down to 5.12 volts, and an operational amplifier 120 connected as a voltage follower supplies buffered 5.12 Volts to the REF+ and $V_{CC}$ inputs of the analog-to-digital converter 30. A National Type No. LM301A operational amplifier is a suitable type for the amplifier 120. A stabilizing and filter capacitor 122 is also connected to the buffer amplifier 120 output.

Since the ADC0816 is an 8-bit converter, the number of quantizing steps is $2^8$ or 256 steps. Hence the quantizing step-size is approximately twenty millivolts/step, and the absolute accuracy of the converter is +1 LSB. Thus forty steps are sufficient to digitize the temperature between 36° C. and 38° C. with a 0.05° C. resolution.

The analog-to-digital converter 30 is interfaced to the microcomputer 12 in a relatively simple manner. Since only one analog signal is being digitized, the address lines of the converter 30 are connected to ground so that the "$IN_0$" analog input of the converter 30 is always selected. Instead of using an external clock generator, the clock input (CLK) of the ADC0816 is connected to the ALE output of the microcomputer 12, which conveniently provides a 400 kHz signal.

The digital output of the analog-to-digital converter 30 is connected directly to the BUS of the 8748. In order to avoid any conflict on the BUS, the converter 30 output is tristated at all times except when the digital data is ready to be outputted to the microcomputer 12. Therefore, the "TRI-STATE" control input is activated only when the "Read" ($\overline{RD}$) output of the 8748 is active, and the A/D address is selected. In this system, the converter 30 is used as a memory mapped I/O device (i.e. the microcomputer 12 accesses the converter 30 as external data memory). In order to minimize the chip count in the circuit, one address line, $A_6$, is dedicated to select the A/D converter 30. Therefore, the microcomputer 12 can read the digital output of the A/D 30 in any of the external data memory locations in which address bit $A_6$ is low.

Two lines from the microcomputer 12 are used to control the timing of the temperature conversion process. If the A/D converter 30 is selected, a pulse on the $\overline{WR}$ line starts the conversion, and a subsequent pulse on the $\overline{RD}$ line enables the digital output of the converter 30 onto the data BUS. The End of Conversion output (EOC) line of the converter 30 is connected to input T0 of the microcomputer 12, which input T0 is testable through program instructions.

Listed hereinafter is a program subroutine "CONV" which serves to convert an analog signal present at channel 0, and return the digital data to the microcomputer accumulator. To start the conversion, the microcomputer 12 writes a random number in external data memory location $80_{16}$. It then waits until the A/D converter 30 acknowledges the end of the conversion to read the digital output of the converter 30 available at location $80_{16}$, and save it in the accumulator.

As stated above, a clock chip 20 is needed in the circuit in order to provide the microcomputer 12 with the time of day information whenever the temperature is measured. It is known that the human body temperature follows a cyclic pattern during the day. Accordingly the temperature reading is adjusted according to the time at which it has been measured, thereby increasing the accuracy of the measurement. Furthermore, the basal body temperature is only valid between approximately 6:00 A.M. and 10:00 A.M. The clock chip 20 is used to create a time window in which the microprocessor 12 is within which the actual time of a temperature reading must lie in order to be accepted as valid.

A suitable clock 20 is an OKI Type No. MSM5832 which is a CMOS clock/calendar integrated circuit. It is microprocessor compatible in the sense that it features a 4-bit I/O data bus, a 4-bit "address" bus, and four control lines. The "address" selects the format of the data in seconds, minutes, hours, day-of-the-week, date, month, or year. The control lines include READ, WRITE, and HOLD lines. The READ line, when activated, enables the time information to be outputted on the data bus 22. The WRITE line, when activated, enables the time information to be sent to the clock chip 20; it can be used to reset the clock chip and adjust it to the correct time. The HOLD line, when activated, stops the internal seconds counter, and thus allows error-free read or write operations. The chip 20 has a low power dissipation of 2.5 milliwatts maximum at $V_{CC}=5$ volts.

The clock chip 20 has an internal oscillator employing an external quartz crystal 124 and external capacitors 126 and 128 connected to $\overline{XT}$ and XT inputs. The clock chip 20 is always powered, and has its $V_{CC}$ input connected directly to the mercury battery 42.

The clock 20 is interfaced directly to the microcomputer 12. Since the microcomputer 12 has many I/O lines available, ten of them are used to interface the MSM5832 directly in order to minimize the logic needed, the chip count, and the power consumption of the circuit. Port 1 of the 8748 is dedicated totally to the four data lines and the three address lines of the clock chip 20 (since the fourth address line is not needed in this application). Three lines of Port 2 are connected to the READ, WRITE, and HOLD lines of the clock chip through the inverters 56, 58 and 60. Thus the lower half of Port 1 is used to transfer data to or from the clock chip 20. The upper half of Port 1 is used to select the "address"(i.e., the data format) of the clock chip 20. Port 2 is used to control the "read" and "write" operations in the clock chip 20.

The Read operation is done in software by the microcomputer 12, and comprises selecting the "address" for the desired format, and then reading the data from the data Bus 22 (Port 1) taking into consideration the expected delay before the data is valid.

The Write operation is also implemented in software by the microcomputer 12. Listed hereinafter is a subroutine TIMESET which sets the clock chip to 8 A.M. whenever the interrupt switch S3 is activated by the user. This program resides in ROM, and should be executed when the power supplying the clock chip goes off (when changing the batteries for example). Since the accuracy of the clock chip is very high and since the "second" information is not utilized, it does not need to be otherwise adjusted.

While in no way intended to limit the scope of the claimed invention, the following table lists suitable values for various components within the instrument, in addition to those specifically described hereinabove, which are also exemplary only.

TABLE OF COMPONENT VALUES

| | Resistors |
|---|---|
| 62, 66, 68 | 4.7 K Ohm each |
| 86 | 2.18 K Ohm |
| 92 | 1000 Ohm |
| 98 | 100 Ohm adjustable |
| 100 | 1330 Ohm |
| 104, 106 | 12.1 K Ohm |
| 108, 110 | 1 Meg. Ohm |
| 116 | 2.97 K Ohm |
| 118 | 100 K Ohm potentiometer |
| | Capacitors |
| 64 | 1 mfd. |
| 78, 80 | 21 pf. |
| 122 | 10 mfd. |
| 126, 128 | 18 pf. |
| | Diodes |
| 84 | National LM385 |
| 112 | 1N4148 |
| 114 | National LM329 |
| | Quartz Crystals |
| 76 | 5.35 MHz |
| 124 | 32768 Hz |

The remainder of the instrument 10 comprises a program stored within non-volatile program memory within the microcomputer 12. The program is effective, in response to operation of the ON/OFF switch S1 to the ON position, to cause the microcomputer 12 to execute a series of instructions for performing the necessary functions. The more important parts of the program are presented in flow chart form as FIGS. 4, 5 and 6, while the entire program is listed in 8048 or 8748 assembly language hereinafter. The software is organized into a main program MAIN, and twelve subroutines. FIG. 4 is a flow chart for program MAIN. Two subroutines, TEMPER and STABLE are presented in flow chart form in FIGS. 5 and 6, respectively, as well as in complete assembly listing form hereinbelow.

Immediately below is a general summary of the program operation, followed by a more detailed description of routines MAIN, TEMPER, and STABLE with reference to FIGS. 4, 5 and 6, in turn followed by an assembly-language listing of the complete program, including all routines.

The program is executed once every day, when the user measures her temperature, until the upward shift in temperature is detected. The execution of the program starts when the Reset ($\overline{RST}$) line of the microcomputer 12 is momentarily pulled low by the capacitor 64 when power is applied. This automatically starts the execution at location 0 of the program memory, which contains an unconditional jump to location $100_{16}$. At this point, the T0 input line of the microcomputer 12 is tested to see if it is the first day of the menstrual cycle or not as indicated by the switch S2. In case the temperature is being taken on the first day, T0 is low, and the registers and counters used in the program are initialized and saved in the CMOS RAM comprising devices 16 and 18.

The program continues by fetching the registers and important memory locations from the CMOS RAM. It then calls subroutine INITIAL which causes the temperature readings during the first three days of the menstrual cycle to be disregarded, since these temperatures are not physically meaningful. Next, subroutine TEMPER is called. This subroutine keeps converting the temperature at ten second intervals until the temperature reaches a stable value. A stable reading is indicated to the user by displaying the temperature reading in degrees on the Liquid Crystal Display 34. The program then causes the time of day information to be read from the clock chip 20, and adjusts the temperature accordingly. It also checks if the temperature value is valid, and if not, it ignores the value, saves the registers and stops the program.

At this point, the temperature value is stored and saved in external RAM 14 for eight days starting at day 4, and until day 11. Then the baseline is computed by retrieving the eight temperatures from external RAM, and averaging them. The reference is then calculated by adding 0.1° C. to the baseline.

Starting at day 12, the CUSUM is calculated every day. If the CUSUM exceeds the decision interval, and if the last three temperatures are above the reference, an acknowledgement signal is displayed to show that a rise in the body temperature has been detected. Specifically, the colon in the LCD display 34 is caused to blink. The program can stop at this point until the start of the next menstrual cycle. However, if the CUSUM does not exceed the decision interval, or if the last three temperatures measured are not all above the baseline, then the program saves all the regisers and important memory locations and waits for the next day.

Subroutine CONVERT controls the analog-to-digital converter 30. It sets the control lines of the A/D for a proper conversion, and stores the digital temperature in register R2.

Subroutine FIVE creates a five-second delay time, by using the Timer feature of the 8748, and another register as a counter.

Subroutine TIMEADJ controls the clock chip 20. It checks if the time at which the temperature is being measured is between 6 A.M. and 10 A.M., by properly manipulating the Read, Hold and address lines. It also adjusts the temperature according to the time of day, by adding 0.1° C. to the temperature for each hour ahead of 10 A.M.

Subroutine TIMESET also controls the clock chip 20. It initializes the time to 8 A.M., by properly maintaining the Write, Hold and address lines. This subroutine is the service routine of an external interrupt, so the user can set the time on the clock chip after a discontinuity in power (i.e., when the batteries are being changed) by operating momentary switch S2 to pull microcomputer 12 Test input T1 low when power is switched on.

The architecture of the 8048 or 8748 microprocessor 12 includes eight general purpose registers within the 64-byte on-chip random-access memory which are directly accessible via program instructions. It is believed that a summary of the usages of these registers in the subject instrument will aid in understanding of the program, and such a summary is presented in the following TABLE, which also indicates which registers contain data which needs to be saved in the external data-saving RAM 14 between program executions.

| TABLE OF REGISTER ASSIGNMENTS | | |
|---|---|---|
| Register | Use | Saved? |
| R0 | Points to address in external RAM where temperature for each day is stored. | Yes |
| R1 | General purpose use by program | No |
| R2 | Temperature returned in this register by subroutine STABLE. | No |
| R3 | General purpose use by program. Reference temperature value stored in this register after calculation on baseline day 8. | Yes |
| R4 | General purpose use by program. CUSUM accumulated in this register commencing on day 12. Initialized to zero on baseline day 8. | Yes |
| R5 | Termed an "NC2 counter" and utilized to count the consecutive decison days to 3. Initialized to zero. | Yes |
| R6 | "Initial counter" utilized to count the first 3 days for which temperature data is disregarded. Initialized at 3, and decremented to zero. | Yes |
| R7 | "Day Counter" utilized to count 8 baseline days. Initialized at 1. | Yes |

While it is believed that the flow charts of FIGS. 4, 5 and 6, as well as the complete assembly-language program listings included herein, will be readily understood by those skilled in the art, it is also believed that a description of the programs with reference to the flow charts of FIGS. 4, 5 and 6 will aid in an understanding and appreciation of the invention.

Since the main program shown in flowchart form in FIG. 4 calls all of the subroutines, either directly or indirectly, the main program of FIG. 4 will be better understood in view of the following summary of two particularly important subroutines, "TEMPER" of FIG. 5 and "STABLE" of FIG. 6.

Referring specifically to FIG. 6, subroutine "STABLE" when called, causes temperature readings to be successively taken, at intervals of approximately ten seconds, and waits until successive temperature readings have stabilized. As may be seen from the assembly language listing herein, subroutine STABLE in turn calls subroutine CONV which actually controls the analog-to-digital converter 30, and returns the temperature as a digital number in register R2.

In FIG. 6, subroutine STABLE begins at box 200. Next, in box 202, an initial thirty-second delay is created to allow insertion of the temperature probe including the thermistor 26 into the oral cavity and the beginning of temperature rise as sensed by the thermistor 26.

Under normal circumstances, equilibrium is not reached in less than thirty seconds.

Next, in box 204, the temperature as sensed by thermistor 26 is converted to a digital value through a call to subroutine CONV. Subroutine CONV returns the digital temperature value in register R2, and subroutine STABLE then transfers the digital temperature reading to register R1.

Next, in box 206, a ten second delay is created and then, in box 208, a temperature reading is again taken, through another call to subroutine CONV. This time, the digital temperature reading is left in register R2.

Next, in decision box 210, the absolute difference of the two temperatures stored registers R1 and R2 is taken, and compared to 0.03° C. If this difference is not less than 0.03° C., then the decision of box 210 is "NO", and the subroutine STABLE goes back to box 204.

If, on the other hand, the test of box 210 is satisfied, then execution proceeds to box 212, which is a call to subroutine DISPLAY, listed in an assembly-language form herein. Subroutine DISPLAY causes the digital temperature reading, which is stored in register R2, to be displayed on the Liquid Crystal Display 34, thus indicating to the user the successful taking of a temperature reading.

Subroutine STABLE then concludes at box 214, with a return to the calling routine.

With reference now to FIG. 5, subroutine TEMPER is shown in flow chart form, beginning with box 300. The purpose of subroutine TEMPER is two-fold. First, subroutine TEMPER causes a temperature reading to be taken and converted to a digital form through a call to subroutine STABLE which, as noted above, in turn calls subroutine CONV. The second, and more significant, purpose of subroutine TEMPER is to establish the predetermined range of temperatures within which the measured temperature must lie in order to be accepted as valid. In accordance with the invention, the predetermined range of valid temperatures comprises one range, for example 36.0° C. to 37.1° C. during the baseline days, and a higher range, for example 36.0° C. to 38.0° C., for days subsequent to the last baseline day.

Accordingly, following the initial box 300, subroutine TEMPER, in box 302, calls subroutine STABLE, described immediately above.

Next, in box 304, subroutine TIMEADJ is called, listed herein in assembly language form only. Subroutine TIMEADJ verifies that the time of the temperature reading is within the four-hour window from 6:00 A.M. to 10:00 A.M., and also adjusts the temperature reading according to the time of day, taking into account the normal 0.1° C. per hour rate of rise expected during the four-hour temperature window. Subroutine TIMEADJ sets an internal flag (flag F1) within the microcomputer 12 in the event the time is outside the four-hour window.

Next, in decision box 306, subroutine TEMPER asks, by checking the status of the flag (F1) whether the time is within the window. If not, an immediate return to the calling routine is made, as indicated by the "NO" line to return box 308.

If, the result in decision box 306 is "YES", then the digital temperature is checked to see whether it is within the predetermined range of valid temperatures.

In decision box 310, the program checks whether the temperature is less than 36.0° C., i.e., whether the temperature is below the predetermined range of valid temperatures. If the answer is "YES", then execution proceeds to box 312 which sets a flag (also internal microcomputer flag F1) to indicate the temperature reading is outside the window.

If the answer in decision box 310 is "NO" then program execution proceeds to decision box 314 which determines whether the upper temperature limit should be that for the eight baseline days (days 4-11) for the days following the last baseline day. For the decision of box 314, the program checks the value of a DAY counter (comprising microcomputer 12 register R7) to see whether the DAY number is less than or equal to 8, indicating the baseline period, or not, indicating days subsequent to baseline period.

If the answer in decision box 314 is "NO", the DAY number is still within the baseline, then execution proceeds to decision box 316, at which the temperature is compared to the upper limit of 37.1° C. If the measured temperature is greater than this upper limit, then the answer in box 316 is "YES", and execution proceeds to box 312 where the flag is set to indicate temperatures outside the predetermined range. If, in decision box 316, the measured temperature is not greater than the upper limit of 37.1° C., then execution proceeds to decision box 318, the condition for which necessarily is not satisfied if the condition for box 314 is not satisfied.

Going back to decision box 314, if the DAY number is in excess of 8, indicating that the particular day is subsequent to the baseline period, then execution proceeds from box 314 directly to decision box 318, which establishes the upper temperature in the higher range.

Referring finally to the MAIN flow chart of FIG. 4, program MAIN is entered at box 400 upon initial power on reset of the instrument.

Next, in decision box 402, the program checks whether it is the first day of a menstrual period by checking the status of testable input T1, the logic status of which is determined by whether the user has closed switch S2 (FIG. 3A). If the answer in box 402 is "YES", indicating the first day, then, in box 404, all registers are initialized as appropriate for day 1.

Following register initializing box 404, or if it is not Day 1, execution proceeds to box 406 which includes calls to subroutines FETCH and INITIAL, both listed in assembly language form only herein. Subroutine FETCH retrieves from the CMOS RAM devices 16 and 18 the data for registers R0 and R3-R7 saved over from the previous day's execution.

Subroutine INITIAL in turn calls subroutine STABLE for a dummy temperature reading the first three days of each menstrual cycle, and sets a flag (internal microcomputer flag F1) to indicate no calculations are to be done based on the dummy temperature reading.

At this point, it is appropriate to mention subroutine SAVER, which is called at box 408 at the end of program MAIN. Subroutine SAVER is the complement to subroutine FETCH, and has for its purpose the saving, at the end of each day's execution, of the contents of registers R0 and R3-R7 in the CMOS RAM devices 16 and 18 for subsequent retrieval by subroutine FETCH.

Following box 408, program MAIN enters box 410 which is a WAIT LOOP within which program execution remains until the instrument is turned off, concluding that day's operation.

Returning to box 406, execution proceeds to decision box 412 wherein the program asks whether the flag (set by subroutine INITIAL) has been set, indicating the particular day is Day 1, 2 or 3 of the menstrual period for which no calculations are to be taken based on the temperature reading. If the answer is "YES", then execution immediately jumps to box 408 to save the contents of the registers.

If, in decision box 412, it is not Day 1, 2 or 3, then, in box 414, subroutine TEMPER, discussed above, is called to obtain a temperature reading.

Next, in decision box 416, the program checks to verify whether both temperature and time are within their respective window and predetermined range. The program does this by checking the status of flag F1 which is set by subroutine TIMEADJ in the event time is outside the window, and is set by subroutine TEMPER in the event temperature is outside the predetermined range. If time and temperature are not within the window, then execution proceeds to box 408 to conclude that day's execution.

If in decision box 416, both time and temperature are within their respective window and predetermined range, indicating a valid temperature reading, then, in box 418, that day's temperature reading is saved in the external CMOS RAM memory and, in box 420, the baseline day counter (initialized at 1) is incremented.

Then, in decision box 422; the baseline day counter is examined to determine whether the baseline day counter has reached or exceeded eight, indicating completion of the eight-day baseline period.

If the answer in box 422 is "NO", then execution jumps to box 408 to conclude that day's execution.

If, the day number is 8 or greater, then program execution proceeds to decision box 424, wherein the program asks whether the day counter is exactly eight. If the answer is "YES", then in box 426 the CUSUM reference is calculated by averaging the daily temperature readings for the eight baseline days, and adding a statistically predetermined minimum change term. In the subject instrument, this predetermined minimum change term is 0.10° C. The reference is stored in register R3 and not thereafter changed.

Following box 426, on baseline day eight program execution then proceeds to box 428 wherein the CUSUM is initialized to 0. The CUSUM is accumulated in microcomputer register R4, and accordingly it is this register which is initialized to 0.

Following box 428, program execution on baseline day 8 jumps to box 408 to conclude execution.

Going back to decision box 424, if DAY is not equal to eight, then the particular day must be a day subsequent to the baseline period. At this point, program execution proceeds to box 430, wherein a new CUSUM is calculated by subtracting the stored reference value (in register R3) from that particular day's temperature reading (stored in register R2), and adding this difference to the CUSUM being accumulated in register R4.

The CUSUM must always be at least 0. Accordingly, in decision box 431, the CUSUM is checked to see whether it is negative and, if negative, in box 432 the accumulated CUSUM is set to 0.

Next, program execution proceeds to decision box 434 to check whether that day's temperature reading (corrected for time of reading) exceeds the reference stored in register R3. This test is needed because one of the criteria in the modified CUSUM test is that, not only must the CUSUM have reached the predetermined decision interval, but the corrected daily temperature readings must on an individual basis each succeed the reference temperature for three consecutive decision days. A counter designated "NC2" is used for this purpose, and is stored in register R5. Counter NC2 is initialized to 0.

If the answer in decision box 434 is "YES", then, in box 436, the counter NC2 is incremented. Otherwise, in box 438, the counter NC2 is cleared to 0, and program execution jumps to box 408 to conclude execution.

Assuming that particular day's temperature reading exceeds the reference temperature, execution proceeds to decision box 440 which checks whether the calculated cumulative sum has reached the statistically predetermined decision interval which, in the subject instrument, is 0.25. If not, then program execution simply proceeds to box 408 and concludes.

If the cumulative sum has reached or exceeded the decision interval, then from box 440 execution proceeds to decision box 442, which checks whether the counter NC2 indicating the number of consecutive days for which corrected daily temperature readings have exceeded the reference temperature is at least equal to three. If not, then the final condition is not satisfied, and program execution jumps to box 408.

If the answer in decision box 442 is "YES", then, in box 444, subroutine "SIGNAL" is called, listed herein in assembly language form only, to display the acknowledgement signal, indicating to the user the beginning of a period of infertility based on the CUSUM algorithm.

With the conditions satisfied, program execution concludes at box 446.

Below is a complete listing of the program software in 8048 or 8748 assembly-language employing conventional mnemonics.

```
;
;
;            CUSUM PROGRAM TO DETECT
;            THE SHIFT IN BASAL BODY
;            TEMPERATURE IN WOMEN.
;
;
             ORG 000H
             JMP MAIN              ;RESET, GO TO MAIN
             ORG 003H
             CALL ONE              ;INTERRUPT VECTOR, GO TO
             JMP TIMESET           ; TIMESET SUBROUTINE.
             ORG 100H
    MAIN:    JT1 START             ;IF NOT FIRST DAY GO TO START
             MOV R7, #1            ;INITIALIZE DAY COUNTER
             MOV R5, #0            ;INITIALIZE NC2 COUNTER
             MOV R0, #61H          ;INITIALIZE POINTER TO RAM
             MOV R6, #3            ;INITIALIZE "INITIAL" COUNTER
             CALL SAVER            ;SAVE REGISTERS IN CMOS RAM
    START:
             EN I                  ;ENABLE INTERRUPT
             MOV R2, #0            ;START, BY DISPLAYING "0"
             CALL DISPLAY          ;
             CALL FETCH            ;RETRIEVE REGISTERS FROM RAM
             CALL INITIAL          ;IGNORE THE FIRST THREE
             JF1 SAVE              ; TEMPERATURES
             CALL TEMPER           ;FETCH VALID TEMPERATURE
             JF1 SAVE              ; AND STORE IT IN R2
             MOV A, R2             ;SAVE TEMPERATURE IN
             MOVX @R0, A           ; CMOS RAM
             INC R7                ;INCREMENT DAY COUNTER
             MOV A, R7             ;IF DAY>=8, GO
             ADD A, #247           ; TO "EIGHT:
             JC EIGHT              ;
             INC R0                ;INCREMENT POINTER TO HAM
             JMP SAVE              ;SAVE REGISTERS
    EIGHT:
             JNZ SR                ;IF DAY>8 GO TO SR
             MOV R4, #0            ;IF DAY=8, CLEAR BASELINE
             MOV R3, #0            ; REGISTERS (DOUBLE PRECISION)
    BLINE:
             MOVX A, @R0           ;FETCH TEMPERATURE FROM RAM
             ADD A, R3             ; AND DO A DOUBLE PRECISION
             MOV R3, A             ; ADDITION OF THE 8 TEMPERATURE
             CLR A                 ; VALUES STORED IN RAM, AND PUT
             ADDC A, R4            ; THE RESULT IN R3 and R4
             MOV R4, A             ;
             DEC R0                ;CHECK IF 8 TEMPERATURES
             MOV A, R0             ; HAVE BEEN ADDED
             ADD A, #0A0H          ;
             JNZ BLINE             ;
             MOV R1, #3            ;INITIALIZE DIV BY 8 COUNTER
    ROT3:    CLR C                 ;BASELINE = RESULT FROM
             MOV A, R4             ; THE PREVIOUS STEP
             RRC A                 ; DIVIDED BY 8
             MOV R4, A             ;
             MOV A, R3             ;
             RRC A                 ;
             MOV R3, A             ;STORE BASELINE IN R3
             DJNZ R1,ROT3          ;
             ADD A, #5             ;REFERENCE = BASELINE + 0.1
             MOV R3, A             ;STORE REFERENCE IN R3
```

|       |                |                                                |
|-------|----------------|------------------------------------------------|
|       | MOV R4, #0     | ;INITIALIZE CUSUM TO 0                         |
|       | JMP SAVE       | ;SAVE REGISTERS                                |
| SR:   | MOV A, R2      | ;CALCULATE NEW CUSUM                           |
|       | ADD A, R4      | ;                                              |
|       | CPL A          | ;                                              |
|       | ADD A, R3      | ;                                              |
|       | JC SRNEG       | ;IF CUSUM<0, GO TO SRNEG                       |
|       | CPL A          | ;                                              |
|       | MOV R4, A      | ;IF CUSUM>0, PUT CUSUM IN R4                   |
|       | JMP CHECK      | ;                                              |
| SRNEG:| MOV R4, #0     | ;REINITIALIZE CUSUM TO 0                       |
|       | MOV A, R2      | ;FETCH TEMPERATURE                             |
|       | CPL A          | ;                                              |
|       | ADD A, R3      | ;IF TEMPERATURE>REFERENCE                      |
|       | JNC TNEG       | ; THEN GO TO TNEG                              |
|       | MOV R5, #0     | ; ELSE NC2 COUNTER=0                           |
|       | JMP SAVE       | ;SAVE REGISTERS                                |
| TNEG: | INC R5         | ;INCREMENT NC2 COUNTER                         |
|       | MOV A, R4      | ;                                              |
|       | ADD A, #243    | ;IF CUSUM<0.25° C.                             |
|       | JNC SAVE       | ; GO TO SAVE                                   |
|       | MOV A, R5      | ;IF (CUSUM>0.25° C.) AND                       |
|       | ADD A, #253    | ; (NC2 COUNTER<3)                              |
|       | JNC SAVE       | ; GO TO SAVE                                   |
|       | CALL DISPLAY   | ;DISPLAY TEMPERATURE                           |
| LOOP: | CALL SIGNAL    | ;GIVE FINAL SIGNAL                             |
|       | JMP LOOP       | ;                                              |
| SAVE: | CALL SAVER     | ;SAVE ALL REGISTERS                            |
|       | CALL ONE       | ;WAIT FOR ONE SECOND                           |
|       | CALL DISPLAY   | ;DISPLAY TEMPERATURE                           |
| STOP: | JMP STOP       | ;WAIT                                          |

;
;
; SUBROUTINE TEMPER
;
;THIS SUBROUTINE CONVERTS A TEMPERATURE
;AND CHECKS IF THIS TEMPERATURE IS VALID.
;
;

|        |                |                                                |
|--------|----------------|------------------------------------------------|
|        | ORG 1D0H       |                                                |
| Temper:| CALL STABLE    | ;CONVERT TEMP. AND SAVE IT IN R2               |
|        | CALL TIMEADJ   | ;ADJUST TEMP. ACCRDING TO TIME                 |
|        | JF1 RLTRN      | ;IF INVALID TIME, RETURN                       |
|        | MOV A, R2      | ;FETCH TEMPERATURE, AND IF                     |
|        | ADD A, #0D2H   | ; IT IS <36° C.                                |
|        | JNC COMPL      | ; GO TO COMPL                                  |
|        | MOV A, R7      | ;FETCH DAY, AND IF                             |
|        | ADD A, #247    | ; IS<=8, GO                                    |
|        | JNC T37        | ; TO "T37"                                     |
|        | MOV A, R2      | ;FETCH TEMPERATURE, AND IF                     |
|        | ADD A, #69H    | ; IT IS >38° C.                                |
|        | JC COMPL       | ; GO TO COMPL                                  |
|        | RETR           | ;                                              |
| COMPL: | CPL F1         | ;F1 IS A FLAG FOR INVALID TEMP.                |
| RETRN: | RETR           | ;                                              |

;
;SUBROUTINE FIVE
;
;THIS SUBROUTINE CREATES A FIVE
;SECOND DELAY LOOP.
;
;

|        |                |                                                |
|--------|----------------|------------------------------------------------|
|        | ORG 2A0H       |                                                |
| FIVE:  |                | ;                                              |
|        | DIS I          | ;                                              |
|        | SEL RB1        | ;                                              |
|        | CLR A          | ;INITIALIZE A TO 0                             |
|        | MOV R0, A      | ;INITIALIZE COUNTER R0 TO 0                    |
|        | MOV T, A       | ;INITIALIZE TIMER TO 0                         |
|        | STRT T         | ;START TIMER                                   |
| LOOP1: | JTF OVER       | ;WAIT FOR 256 CYCLES (80 MICROSEC              |
|        | JMP LOOP1      | ; EACH) AND GO TO "OVER"                       |
| OVER:  | INC R0         | ;WAIT FOR 256 CYCLES OF                        |
|        | MOV A, R0      | ; 20 MSEC. EACH THEN                           |
|        | JNZ LOOP1      | ; PROCEED.                                     |
|        | STOP TCNT      | ;STOP TIMER                                    |
|        | SEL RB0        | ;                                              |
|        | EN I           | ;                                              |
|        | RETR           | ;                                              |

;

```
;SUBROUTINE CONV
;
;THIS SUBROUTINE CONTROLS THE A/D CONVERTER
;AND RETURNS THE DIGITAL TEMPERATURE IN R2.
;
;
            ORG 290H
CONV:
            SEL RB1                 ;
            MOV R1, #0AOH           ;SELECT A/D ADDRESS
            MOVX @R1, A             ;START CONVERTING
CWAIT:      JNT0 CWAIT              ;WAIT FOR END OF CONVERSION
            MOVX A, @RI             ;PUT DIGITAL DATA IN A
            SEL RB0                 ;
            MOV R2, A               ;SAVE DIGITAL TEMPERATURE IN R2
            RETR                    ;
;
;
;SUBROUTINE STABLE
;
;THIS SUBROUTINE KEEPS CONVERTING THE
;TEMPERATURE UNTIL IT STABILIZES, AND
;THEN IT DISPLAYS THE TEMPERATURE.
;
;
            ORG 200H
STABLE:
            SEL RB0                 ;
            MOV R1, #6              ;WAIT FOR 30 SECONDS
            CALL FIVE               ; BEFORE STARTING TO
            DJNZ R1, STABLE         ; MONITOR THE TEMPERATURE
REPEAT:     CALL CONV               ;CONVERT TEMP AND SAVE IT IN R2
            MOV A, R2               ;SAVE TEMPERATURE IN R1
            MOV R1, A               ;
            CALL FIVE               ;CREATE A 5 SEC. DELAY TIME
            CALL FIVE               ;CREATE A 5 SEC. DELAY TIME
            CALL CONV               ;CONVERT TEMP AND SAVE IT IN R2
            MOV A, R2               ;TAKE THE ABSOLUTE DIFFERENCE
            CPL A                   ; OF THE TWO TEMPERATURES
            ADD A, R1               ;
            JC POS                  ;
            CPL A                   ;
POS:        ADD A, #0FEH            ;IF DIFF>.03° C., GO BACK
            JC REPEAT               ; TO "REPEAT"
            CALL DISPLAY            ;
            RETR                    ;
;
;
;SUBROUTINE INITIAL
;
;THIS SUBROUTINE IN TURN CALLS SUBROUTINE STABLE
;FOR A DUMMY TEMPERATURE READING DURING THE FIRST
;THREE DAYS OF EACH MENSTRUAL CYCLE AND SETS F1 to 1
;SO NO CALCULATIONS ARE DONE BASED ON THE FIRST
;THREE TEMPERATURE READINGS.
            ORG 1C0H
INITIAL:
            CLR F1                  ;SET F1 to 0
            MOV A, R6               ;FETCH INITIAL COUNTER
            ADD A, #0               ;SET FLAGS
            JZ RETURN               :IF INITIAL COUNTER=0, GO TO RETU
            DEC R6                  ;DECREMENT INITIAL COUNTER
            CALL STABLE             ;CALL SUBROUTINE STABLE
            CPL F1                  ;COMPLEMENT F1 to 1
RETURN:     SEL RB0                 ;
            RETR                    ;
;
;
;SUBROUTINE FETCH
;
;THIS SUBROUTINE FETCHES ALL THE REGISTERS
;FROM THE CMOS RAM.
;
;
            ORG 1A0H
ETCH:       MOV R1, #70H            ;
            MOVX A, @R1             ;
            MOV R0, A               ;RETRIEVE R0
            INC R1                  ;
            MOVX A, R1              ;
            MOVE R3, A              ;RETRIEVE R3
```

```
                INC R1                  ;
                MOVX A, @R1             ;
                MOV R4, A               ;RETRIEVE R4
                INC R1                  ;
                MOVX A, @R1             ;RETRIEVE R5
                INC R1                  ;
                MOVX A, @R1             ;
                MOV R7, A               ;RETRIEVE R7
                RETR                    ;
;
;SUBROUTINE SAVER
;
;THIS SUBROUTINE SAVES ALL THE REGISTERS
;IN THE CMOS RAM.
;
;
                ORG 2COH
SAVER:          MOV R1, #70H            ;
                MOVA,RO                 ;
                MOVX @R1, 4             ;SAVE R0 IN CMOS RAM
                INC R1                  ;
                MOV A, R3               ;
                MOVX @R1, A             ;SAVE R3 IN CMOS RAM
                INC R1                  ;
                MOV A, R4               ;
                MOVX @R1, A             ;SAVE R4 IN CMOS RAM
                INC R1                  ;
                MOV A, R5               ;
                MOV @R1, A              ;SAVE R5 IN CMOS RAM
                INC R1                  ;
                MOV A, R6               ;
                MOVX @R1, A             ;SAVE R6 IN CMOS RAM
                INC R1                  ;
                MOV A, R7               ;
                MOVX @R1, A             ;SAVE R7 IN CMOS RAM
                RETR                    ;
;
;SUBROUTINE TIMEADJ
;
;THIS SUBROUTINE ADJUSTS THE TEMPERATURE
;ACCORDING TO THE TIME OF THE DAY.
;
;
                ORG 230H
TIMEADJ:
                CLR F1                  ;
                ANL P2, #OEFH           ;HOLD=1
                MOV R1, #20H            ;WAIT FOR 150 MICROSECONDS
DLAY:           DJNZ R1,DLAY            ;
                ANL P2, #ODFH           ;READ=1
                ORL P1, #50H            ;SEL H10 (ADDR=0101)
                ANL P1, #ODFH           ;
                ORL P1, #OFH            ;PORT 1 IS INPUT PORT
                NOP                     ;
                NOP                     ;
                NOP                     ;
                IN A, P1                ;FETCH H10
                ANL A, #03H             ;UNMASK H10 DATA
                JNZ BAD                 ;IF H10 NOT EQUAL TO 0 GO TO BAD
                ORL P1, #4FH            ;SELECT H1 (ADDR=0100)
                ANL P1, #OCFH           ;
                ORL P1, #OFH            ;PORT 1 IS INPUT PORT
                NOP                     ;
                NOP                     ;
                NOP                     ;
                IN A, P1                ;FETCH H1
                ORL P2, #30H            ;READ = HOLD = 0
                ANL A, #OFH             ;MASK OFF HIGH BYTE
                ADD A, #OF7H            :ADD 247 to H1
                JZ NINE                 ;IF H1=9, GO TO "NINE"
                INC A                   ;
                JZ EIT                  ;IF H1=8, GO TO "EIT"
                INC A                   ;
                JZ SEVEN                ;IF H1=7, GO TO "SEVEN"
                INC A                   ;
                JZ SIX                  ;IF H1=6, GO TO "SIX"
BAD:            ORL P2, #30H            ;READ = HOLD = 0
                CPL F1                  ;
                RETR                    ;
SIX:            MOV A, R2               ;
```

|  |  |  |
|---|---|---|
| | ADD A, #7 | ;ADD 0.1° C. TO TEMPERATURE |
| | MOV R2, A | ; |
| SEVEN: | MOV A, R2 | ; |
| | ADD A, #7 | ;ADD 0.1° C. TO TEMPERATURE |
| | MOV R2, A | ; |
| EIT: | MOV A, R2 | ; |
| | ADD A, #7 | ;ADD 0.1° C. TO TEMPERATURE |
| | MOV R2, A | ; |
| NINE: | MOV A, R2 | ; |
| | ADD A, #7 | ;ADD 0.1° C. TO TEMPERATURE |
| | MOV R2, A | ; |
| | RETR | ; |

;
;SUBROUTINE TIMESET
;
;THIS SUBROUTINE INITIALIZES THE CLOCK CHIP
;TO 8:00 A.M. WHEN SWITCH S3 TRIGGERS INTERRUPT.
;
;

|  |  |  |
|---|---|---|
| | ORG 350H | |
| TIMESET: | | |
| | ANL P2, #0EFH | ;HOLD=1 |
| | MOV R1, #20H | ; |
| DELAY: | DJNZ R1,DELAY | ;WAIT FOR 150 MICROSECONDS |
| | ORL P2, #30H | ;MI1O = 0 (ADDR=0011) |
| | ANL P1, #0BOH | ; |
| | NOP | |
| | ANL P1, #0BFH | ;WRITE = 1 |
| | NOP | ; |
| | ORL P2, #40H | ;WRITE = 0 |
| | NOP | ; |
| | ORL P1, #20H | ;MI1=0 (ADDR=0010) |
| | ANL P1, #0AOH | ; |
| | NOP | |
| | ANL P2, #0BFH | ;WRITE = 1 |
| | NOP | ; |
| | ORL P2, #40H | ;WRITE = 0 |
| | NOP | ; |
| | ORL P1, #58H | ;H1O = 0 (ADDR=0101) |
| | ANL P1, #0D8H | ; |
| | NOP | |
| | ANL P2, #0BFH | ;WRITE = 1 |
| | NOP | ; |
| | ORL P2, #40H | ;WRITE = 0 |
| | NOP | ; |
| | ORL P1, #48H | ;H1 = 8(ADDR=0100) |
| | ANL P1, #0C8H | ; |
| | NOP | |
| | ANL P2, #0BFH | ;WRITE = 1 |
| | NOP | ; |
| | ORL P2, #40H | ;WRITE = 0 |
| | NOP | ; |
| | ORL P2, #10H | ;HOLD = 0 |
| | RETR | ; |

;
;SUBROUTINE DISPLAY
;
;THIS SUBROUTINE DISPLAYS THE
;TEMPERATURE ON THE LCD.
;
;

|  |  |  |
|---|---|---|
| | ORG 300H | |
| | MOV A, R2: | ;FETCH TEMPERATURES |
| | ANL A, #0FH | ;MASK OFF UPPER HALF |
| | | ;SELECT DIGIT 4 |
| | MOV R1, #0COH | ;LCD ADDRESS |
| | MOV @R1, A | ;OUTPUT DATA TO DECODER-DRIVER |
| | MOV A, R2 | ;FETCH TEMPERATURE |
| | SWAP A | ; |
| | ANL A, #0FH | ;MASK OFF LOWER HALF |
| | ORL A, #10H | ;SELECT DIGIT 3 |
| | MOV R1, #0COH | ; |
| | MOV @R1, A | ;OUTPUT DATA TO DECODER-DRIVER |
| | RETR | |

;
;SUBROUTINE SIGNAL
;
;THIS SUBROUTINE DISPLAYS THE
;ACKNOWLEDGEMENT SIGNAL BY

```
;FLASHING DISPLAY COLON
;
;
            ORG 320H
SIGNAL:     CLR A                    ;
            ORL A, #20H              ;SELECT DIGIT 3
            MOV R1, #OCOH            ;LCD ADDRESS
            MOVX @R1, A              ;SEND DATA TO DECODER-DRIVER
            CALL ONE                 ;WAIT FOR ONE SECOND
            CLR A                    ;
            ORL A, @21H              ;SELECT DIGIT 3
            MOV R1, #OCOH            ;LCD ADDRESS
            MOVX #R1, A              ;SEND "1" TO DECODER-DRIVER
            CALL ONE                 ;WAIT FOR ONE SECOND
            RETR                     ;
;
;
;SUBROUTINE ONE
;
;THIS SUBROUTINE CREATES A ONE
;SECOND DELAY TIME.
;
;
            ORG 340H
ONE:        SEL RB1                  ;
            MOV R2, #OFFH            ;FIRST COUNTER
WAIT1:      MOV R3, #OFFH            ;SECOND COUNTER
WAIT2:      DJNZ R3,WAIT2            ;LOOP 256 TIMES
            DJNZ R2,WAIT1            ;LOOP 256 TIMES
            SEL RB0                  ;
            RETR                     ;
            END                      ;
;
;
;PROGRAM COPYRIGHT 1981 UNIVERSITY OF FLORIDA
;
```

While a specific embodiment of the invention has been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A low power, microprocessor-based instrument for indicating shift in basal body temperature in women, said instrument comprising:

a battery power supply having a first supply line providing a continous voltage, an ON/OFF switch, and at least one second supply line providing a switched voltage when said ON/OFF switch is ON;

a microcomputer including a central processing unit, a non-volatile program memory connected to said central processing unit and powered from said switched second supply line, and a data-saving random-access memory having low power consumption connected to said central processing unit and powered from said continuous first supply line;

a digital clock circuit having low power consumption and powered from said continuous first supply line, said digital clock circuit connected to supply data to said central processing unit;

a temperature data acquisition subsystem powered from said switched second supply line and including a temperature sensor and an analog-to-digital converter, said data acquisition system connected to supply data to said central processing unit;

a user display device including a temperature reading indicator and a condition satisfied indicator, said user display device connected to receive data from said central processing unit; and a program stored within said non-volatile program memory effective, in response to operation of said ON/OFF switch to the ON position, to cause said microcomputer to execute a series of instructions for acquiring basal body temperature data on a daily basis, performing a cumulative sum statistical test, and signalling when a statistically-significant shift in basal body temperature has occurred, said instructions effecting the steps of:

taking a daily temperature reading by directing said temperature data acquisition subsystem to acquire successive temperature data at predetermined intervals, and comparing each temperature datum with a previous datum until a substantially stable reading is indicated;

directing said user display device to indicate a stable temperature reading has been acquired;

verifying whether the temperature reading is within a predetermined range of valid temperatures and disregarding if outside the predetermined range of valid temperatures;

obtaining temperature reading time data from said digital clock circuit and verifying whether the temperature reading time is within a predetermined time window including normal waking time and within which temperature readings should be taken so as to be valid, and disregarding if outside the predetermined time window;

calculating a corrected temperature reading as a function of the temperature reading time by effectively decreasing the temperature reading by approximately 0.1° C. per hour starting from the beginning of the predetermined time window;

accumulating corrected temperature readings for a predetermined number of baselines days, and calculating an average temperature for the baseline days;

adding a statistically predetermined minimum change term to the baseline average temperature to calculate a reference temperature;

for each day subsequent to the last baseline day, calculating the cumulative sum of positive deviations of the corrected daily temperature readings over the reference temperature;

for each day subsequent to the last baseline day, determining whether a final condition has been satisfied, the final condition being satisfied when both the calculated cumulative sum has reached a statistically predetermined decision interval and the corrected daily temperature readings have each exceeded the reference temperature for a predetermined number of consecutive decision days;

if the final condition is satisfied, directing said user display device to indicate condition satisfied, and storing in said data saving random-access memory prior to the end of program execution for each day all necessary data to execute the series of instructions on the following day, the necessary data including a count of the baseline days up to the predetermined number of baseline days, the calculated reference temperature, the cumulative sum, and a count of the consecutive decision days up to the predetermined number of consecutive days.

2. An instrument in accordance with claim 1, wherein said program instructions are further effective to cause the temperature readings for an initial predetermined number of days to be disregarded.

3. An instrument in accordance with claim 1, wherein said program instructions are initially effective to retrieve from said data-saving random-access memory the necessary data from the previous day to execute the series of instructions on the particular day of use.

4. An instrument in accordance with claim 2, wherein the initial predetermined number of days for which temperature readings are disregarded is three days;

the predetermined number of baseline days is eight days; and the predetermined number of consecutive decision days is three days.

5. An instrument is accordance with claim 1, wherein the predetermined range of valid temperatures comprises one range during the baseline days, and a higher range for each day subsequent to the last baseline day.

6. An instrument in accordance with claim 4, wherein the predetermined range of valid temperatures is approximately from 36.0° C. to 37.1° C. during the baseline days, and approximately from 36.0° C. to 38.0° C. for each day subsequent to the last baseline day;

the predetermined time window is approximately four hours from 6:00 AM to 10:00 AM;

the statistically predetermined minimum change term is 0.1° C.; and the statistically predetermined decision interval is 0.25° C.

* * * * *